United States Patent [19]

Berg et al.

[11] Patent Number: 5,225,050
[45] Date of Patent: Jul. 6, 1993

[54] SEPARATION OF N-HEXANE FROM VINYL ACETATE BY EXTRACTIVE DISTILLATION

[75] Inventors: Lloyd Berg, 1314 S. Third Ave., Bozeman, Mont. 59715; Randi W. Wytcherley, Bozeman, Mont.

[73] Assignee: Lloyd Berg, Bozeman, Mont.

[21] Appl. No.: 991,348

[22] Filed: Dec. 15, 1992

[51] Int. Cl.$^5$ .......................... B01D 3/40; C07C 7/08; C07C 67/54
[52] U.S. Cl. ........................................ 203/57; 203/58; 203/60; 203/63; 203/62; 203/65; 560/248; 585/860; 585/864; 585/865; 585/866
[58] Field of Search ...................... 203/57, 58, 60, 62, 203/63, 65, DIG. 10; 560/248; 585/860, 864, 865, 866

[56] References Cited

U.S. PATENT DOCUMENTS

| | | | |
|---|---|---|---|
| 2,171,795 | 9/1939 | Kautter | 203/65 |
| 3,394,057 | 7/1968 | Miller et al. | 560/248 |
| 3,691,021 | 9/1972 | Feldman et al. | 203/65 |
| 3,736,236 | 5/1973 | DiFiore et al. | 560/248 |
| 4,897,161 | 1/1990 | Berg et al. | 203/51 |
| 4,925,533 | 5/1990 | Berg | 203/51 |
| 5,106,460 | 4/1992 | Berg | 203/60 |

Primary Examiner—Wilbur Bascomb, Jr.

[57] ABSTRACT

Hexane cannot be removed from hexane - vinyl acetate mixtures by distillation because of the minimum boiling azeotrope. Hexane can be readily removed from vinyl acetate by extractive distillation. Typical effective agents are phenol, 1-nitropropane and benzyl alcohol.

1 Claim, No Drawings

SEPARATION OF N-HEXANE FROM VINYL ACETATE BY EXTRACTIVE DISTILLATION

FIELD OF THE INVENTION

This invention relates to a method for separating n-hexane from vinyl acetate using certain higher boiling liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate greater and thus requires either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Extractive distillation would be an attractive method of effecting the separation of n-hexane from vinyl acetate if agents can be found that (1) will create a large apparent relative volatility between n-hexane and vinyl acetate and (2) are easy to recover from vinyl acetate, that is, form no azeotrope with vinyl acetate and boil sufficiently above vinyl acetate to make the separation by rectification possible with only a few theoretical plates.

Extractive distillation typically requires the addition of an equal amount to twice as much extractive agent as the hexane - vinyl acetate on each plate of the rectification column. The extractive agent sould be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Celcius degrees or more difference. It is also desirable that the extractive agent be miscible with overhead products otherwise it will form a two phase azeotrope with them and some other method of separation will have to be employed. n-Hexane, B.P.=68.7°C. and vinyl acetate, B.P.=72.7° C. form a minimum boiling azeotrope containing 15% vinyl acetate and are thus impossible to separate by conventional rectification. Their relative volatility is 1.0. Table 1 shows the relative volatility required to get 99% purity. For an agent giving a relative volatility of 3.0, only twelve actual plates are required.

TABLE 1

Theoretical and Actual Plates Required vs. Relative Volatility for n-Hexane - Vinyl Acetate Separation

| Relative Volatility | Theoretical Plates Required At Total Reflux, 99% Purity | Actual Plates Required, 75% Eff. |
|---|---|---|
| 1.20 | 50 | 67 |
| 1.5 | 23 | 31 |
| 2.0 | 13 | 17 |
| 2.5 | 10 | 13 |
| 3.0 | 9 | 12 |

OBJECTIVE OF THE INVENTION

The object of this invention is to provide a process or method of extractive distillation that will enhance the relative volatility of n-hexane from vinyl acetate in their separation in a rectification column. It is a further object of this invention to identify organic compounds which in addition to the above constraints, are stable, can be separated from vinyl acetate by rectification with relatively few theoretical plates and can be recycled to the extractive distillation column and reused with little decomposition.

SUMMARY OF THE INVENTION

The objects of this invention are provided by a process for separating n-hexane from vinyl acetate which entails the use of certain organic compounds as the agent in extractive distillation.

DETAILED DESCRIPTION OF THE INVENTION

We have discovered that certain organic compounds will greatly improve the relative volatility of n-hexane to vinyl acetate and permit the separation of n-hexane from vinyl acetate by rectification when employed as the agent in extractive distillation.

TABLE 2

Effective Extractive Distillation Agents

| Compounds | Relative Volatility |
|---|---|
| Phenol | 2.9 |
| o-Cresol | 2.65 |
| m-Cresol | 2.2 |
| p-Cresol | 2.55 |
| 2-tert. Butyl phenol | 1.8 |
| 2,4-di-tert. Butyl phenol | 1.4 |
| 2,6-Dimethyl phenol | 1.85 |
| Benzyl alcohol | 1.35 |
| Isopropyl phenol | 3.5 |
| Ethyl valerate | 1.35 |
| 1-Propanol | 1.2 |
| Cyclopentanone | 1.4 |
| Dimethyl carbonate | 1.35 |
| 4-Ethyl phenol | 1.9 |
| Nitrobenzene | 1.35 |
| 2-Nitropropane | 1.3 |
| 1-Nitropropane | 1.7 |
| Nitroethane | 3.5 |

Table 2 lists the compounds that we have found to be effective. They are phenol, 0-cresol, m-cresol, p-cresol, 2-tert. butyl phenol, 2,4-di-tert.butylphenol, 2,6-dimethyl phenol, 4-ethyl phenol, benzyl alcohol, 1- propanol, ethyl valerate, isopropyl phenol, cyclopentanone, dimethyl carbonate, nitrobenzene, nitroethane, 1 nitropropane and 2-nitropropane.

THE USEFULNESS OF THE INVENTION

The usefulness or utility of this invention can be demonstrated by referring to the data presented in Tables 1 and 2. All of the successful agents show that hexane can be separated from vinyl acetate by means of extractive distillation in a rectification column and that the ease of separation as measured by relative volatility is considerable.

WORKING EXAMPLES

EXAMPLE 1

One hundred grams of the hexane - vinyl acetate azeotrope and 50 grams of phenol were charged to an Othmer type vapor-liquid equilibrium still and refluxed for five hours. Analysis of the vapor and liquid by gas chromatography gave a vapor composition of 93.1% hexane, 6.9% vinyl acetate and a liquid composition of 82.1% hexane, 17.9% vinyl acetate. This indicates a relative volatility of 2.9.

EXAMPLE 2

One hundred grams of the hexane - vinyl acetate azeotrope and 50 grams of nitroethane were charged to the vapor-liquid equilibrium still and refluxed for 12 hours. Analysis gave a vapor composition of 96% hexane, 13% vinyl acetate. This indicates a relative volatility of 3.5.

We claim:

1. A method for recovering hexane from a mixture of hexane and vinyl acetate which comprises distilling a mixture of hexane and vinyl acetate in a rectification column in the presence of about one part of an extractive agent per part of hexane - vinyl acetate mixture, recovering the hexane as overhead product and obtaining the vinyl acetate and the extractive agent from the stillpot, wherein said extractive agent comprises one material selected from the group consisting of phenol, o-cresol, m-cresol, p-cresol, 4-ethyl phenol, 2-tert. butyl phenol, 2,4-di-tert.butyl phenol, 2,6-dimethyl phenol, benzyl alcohol, isopropyl phenol, ethyl valerate, 1-propanol, cyclopentanone, dimethyl carbonate, nitrobenzene, nitroethane, 1-nitropropane and 2-nitropropane.

* * * * *